(12) United States Patent
Gobbini et al.

(10) Patent No.: US 6,384,250 B2
(45) Date of Patent: May 7, 2002

(54) PROCESS FOR THE PREPARATION OF (E,Z) 3-(2-AMINOETHOXYIMINO)-ANDROSTANE-6, 17-DIONE AND ITS ANALOGUES

(75) Inventors: Mauro Gobbini, Mercallo; Giulio Carzana, Milan; Simona Sputore, Meda, all of (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/852,265

(22) Filed: May 10, 2001

(30) Foreign Application Priority Data

May 17, 2000 (IT) ........................... RM00A0266

(51) Int. Cl.$^7$ ................................. C07J 41/00
(52) U.S. Cl. ........................................ 552/520
(58) Field of Search ........................... 552/520

(56) References Cited

U.S. PATENT DOCUMENTS 5,914,324 A * 6/1999 De Munari et al. ......... 514/178

* cited by examiner

Primary Examiner—Barbara P. Badio
(74) Attorney, Agent, or Firm—Nixon & Vanderhye

(57) ABSTRACT

An improved process is described for the preparation of compounds with general formula (I) and particularly for the preparation of the compound (E,Z) 3-(2-aminoethoxyimino)-androstane-6,17-dione, in which n=1 and $R^1=R^2=H$ (I)

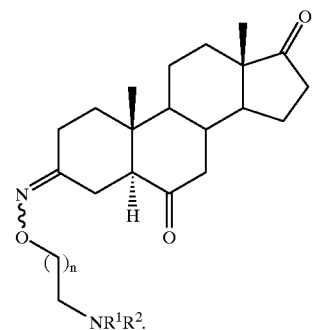

3 Claims, No Drawings

PROCESS FOR THE PREPARATION OF (E,Z) 3-(2-AMINOETHOXYIMINO)-ANDROSTANE-6, 17-DIONE AND ITS ANALOGUES

The subject matter of the invention described herein is an improved process for the preparation of compounds with general formula (I) and in particular of compound (E,Z) 3-(2-aminoethoxyimino)-androstane-6,17-dione (hereinafter referred to as PST 2744) and their pharmaceutically acceptable salts,

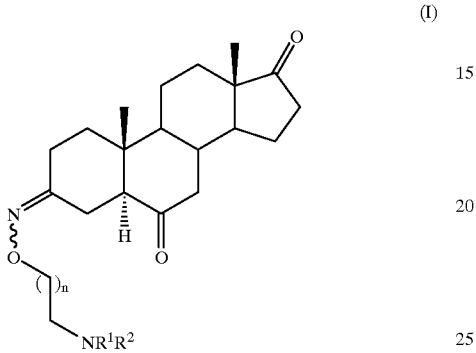

(I)

in which:

n=1–3; $R^1$ and $R^2$, which may be the same or different, are hydrogen or alkyl $C_1$–$C_3$ or together form a 5 or 6 term saturated heterocycle, optionally containing a second heteroatom selected from the group consisting of oxygen, sulphur or nitrogen.

The formula (I) compound in which n=1 and $R^1=R^2=H$ is PST 2744; it is a known compound, endowed with positive inotropic activity at the cardiovascular system level, and is therefore a useful agent in the treatment of heart failure.

European Patent Application EP 0825197 (Sigma-Tau Industrie Farmaceutiche Riunite) discloses PST 2744 and its analogues included in formula (I) above and in addition describes a process for their preparation; PST 2744 is described in the example of preparation no. 7.

The process for the preparation of PST 2744 according to the method described in EP 0825197 is indicated in the following reaction diagram,

DIAGRAM 1

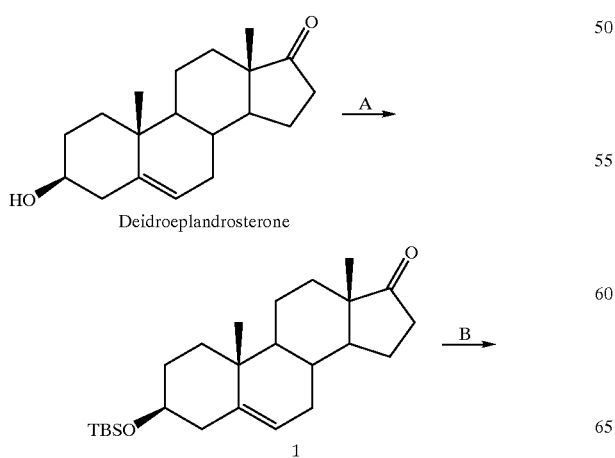

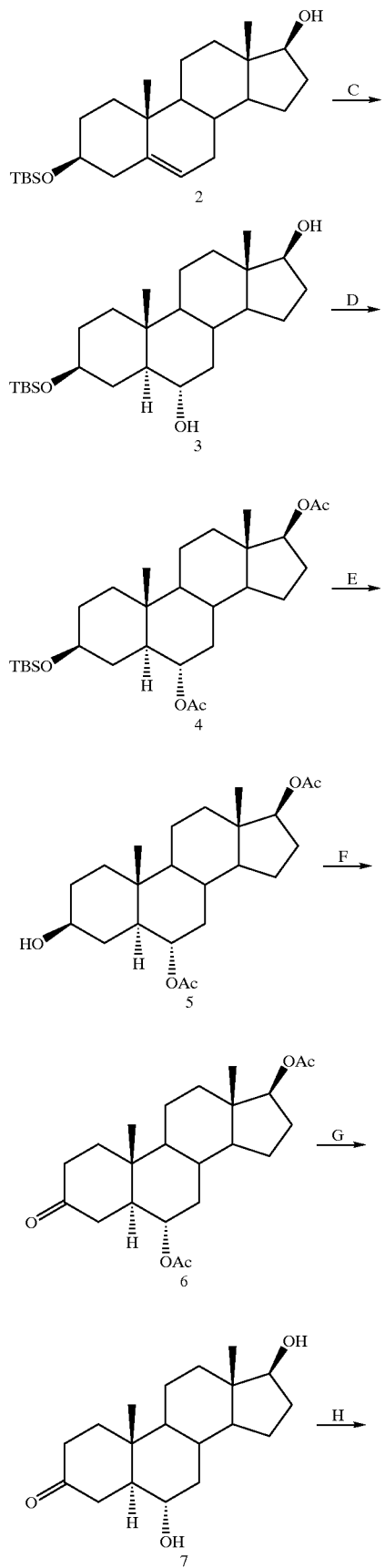

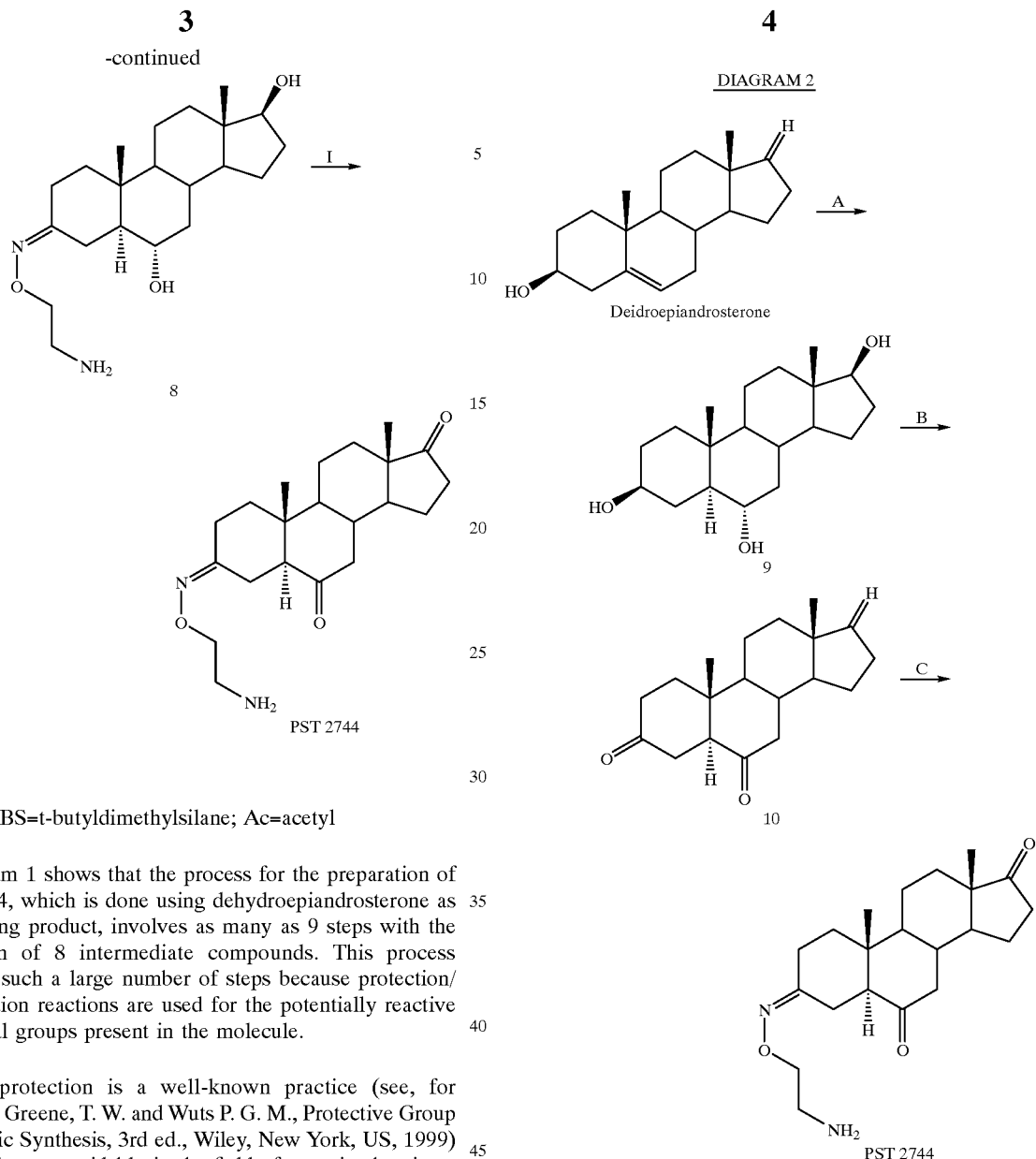

where: TBS=t-butyldimethylsilane; Ac=acetyl

Diagram 1 shows that the process for the preparation of PST 2744, which is done using dehydroepiandrosterone as the starting product, involves as many as 9 steps with the formation of 8 intermediate compounds. This process involves such a large number of steps because protection/deprotection reactions are used for the potentially reactive functional groups present in the molecule.

Such protection is a well-known practice (see, for example: Greene, T. W. and Wuts P. G. M., Protective Group in Organic Synthesis, 3rd ed., Wiley, New York, US, 1999) and is often unavoidable in the field of organic chemistry, but with the drawback that the introduction and subsequent removal of each protective group means lengthening the synthesis process by two steps, with obvious increases in terms both of execution times and costs.

The PST 2744 preparation process described in EP 0825197 is carried out by performig chromatographic purifications of the intermediate products.

An improved process has now been found, and this is the subject matter of the invention described herein, for the preparation of compounds with general formula (I), particularly PST 2744, which avoids the use of protective groups in the various synthesis steps, with a substantial reduction of the number of steps and purifications, and with a substantial reduction of production costs.

The process according to the invention described herein is indicated in the following reaction diagram by way of an example as far as PST 2744 is concerned.

This process comprises the steps of:
(a) introducing a hydroxyl group in position 6α of the steroid skeleton and at the same time reducing the ketone function in position 17, obtaining derivative 9 from dehydroepiandrosterone;
(b) oxidating simultaneously the three hydroxyl groups present in derivative 9, obtaining derivative 10;
(c) selectively oximating the ketone group in position 3 of derivative 10 obtaining PST 2744, preferably in a salified form.

It is perfectly clear that the process according to the invention described herein applies to all formula (I) compounds, which differ from one another in the aminoalkyl chain bound to the oxime group in position 3. Given that the addition of the amine aminoalkoxy chain to ketone group 3, to yield the corresponding oximic derivative is analogous to the reaction described in EP 0825197, the process according to the invention, as exemplified for PST 2744 and regarding the transformations on the steroid nucleus, is applicable by analogy to all formula (I) compounds, as described above.

Any minor changes made to the reactions exemplified (solvents, molar ratios, reaction controls) are thoroughly obvious and immediate to the technician with average experience in the sector, on the basis of his or her own general knowledge alone.

The advantage of the process according to the invention indicated in Diagram 2 can be immediately perceived on comparing it with the process described in EP 0825197 and indicated in Diagram 1.

Moreover, the process according to the invention described herein takes place with optimum selectivity of oximation of the ketone group in position 3, to yield the compound desired, despite the presence of two other ketone groups in positions 6 and 17.

As has been said, the process according to the invention described herein is characterised by the lack of the use of protective groups. In fact, Diagram 2 shows that from the starting compound, dehydroepiandrosterone, intermediate 10 is obtained in two steps, completely skipping intermediates 1–7 indicated in Diagram 1, in which the protective groups are introduced in steps A and D to yield intermediates 1 and 4, and are then removed in steps E and G to give intermediates 5 and 7.

The reaction conditions used in the process which is the subject matter of the invention described herein, with reference to Diagram 2, are:

Step A: ation of the double bond present in position 5 and reduction of the ketone in position 17 of the dehydroepiandrosterone. For this reaction we use borane (both as a monomer and as the diborane dimer), 9-BBN, disiamylborane or texylborane, both in the free form and as complexes with other substances such as, for example, tetrahydrofuran, dimethylsulphur or bases such as, for example, ammonia, dimethylamine, triethylamine, and pyridine. In particular, the borane can be added to the reaction mixture in the form of a complex with tetrahydrofuran or dimethylsulphur, or can be generated in situ by reaction between sodium borohydride and acetic acid or between sodium borohydride and a Lewis acid, such as, for example, borotrifluoride etherate; or, lastly, it may be generated, in the way previously described, in an environment external to the reaction mixture and can be introduced into said mixture. The reaction is done at a temperature ranging from −10° C. to the boiling temperature of the reaction mixture, for a period of time ranging from one to five hours.

The subsequent oxidation of the alkylboranes obtained can be accomplished, for example, with $H_2O_2$/NaOH, with sodium perborate or other alkaline perborates added in aqueous solution to the reaction mixture. The reaction is done at a temperature ranging from −10° C. to the boiling temperature of the reaction mixture, for a time period ranging from 10 to 24 hours. The final product is purified by crystallisation by solvents such as ethyl acetate, methanol, ethanol, isopropanol, acetone, water or mixtures of the same.

Step B: oxidation of the three hydroxyl functions present in compound 9. This oxidation is carried out with oxidants such as chromium oxide in the presence of sulphuric acid and water (Jones reagent) in acetone, at a temperature ranging from −10° C. to the boiling temperature of the reaction mixture; with tetrapropyl-ammonium perruthenate as the oxidant in catalytic amounts and N-methylmorpholine N-oxide as the stoichiometric oxidant, in ethylene chloride or acetonitrile or mixtures of these solvents, optionally in the presence of molecular sieves, at a temperature ranging from −10° C. to the boiling temperature of the reaction mixture; ruthenium tetroxide as the oxidant in catalytic amounts, generated in situ from a stoichiometric oxidant, which can be sodium bromate, sodium hypochlorite or an alkaline periodate, such as sodium periodate, starting from ruthenium hydrate dioxide or ruthenium chloride, in solvents such as acetone, acetonitrile/carbon tetrachloride/water, acetonitrile/ chloroform/water, acetonitrile/methylene chloride/water, ethyl acetate/acetonitrile/water in variable proportions, at a temperature ranging from −10° C. to the boiling temperature of the reaction mixture.

This oxidation reaction described in step B is carried out for a period of time ranging from 0.5 to 24 hours, also depending on the type of oxidant used.

Step C: reaction between triketone 10 and 2-aminoethoxyamine. The reaction is carried out adding the base in salified form or as a free base dissolved in a mixture of solvents such as dioxane, tetrahydrofuran, water or homogeneous mixtures of the same to the reaction mixture containing the triketone in the same solvents as for the base, optionally in the presence of buffer solutions; the pH of the solution may range from approximately 2 to approximately 10 depending on whether or not buffer solutions are used; the reaction temperature ranges from −10° C. to the boiling temperature of the reaction mixture and the time period ranges from 0.5 to 12 hours.

The reaction product is isolated for treatment with solvents such as tetrahydrofuran, ethyl alcohol, isopropyl alcohol, ethyl acetate or mixtures of the same. The reaction product can be isolated as a free base or, preferably, as a salt with inorganic acids such as hydrochloric or sulphuric acid or with organic acids such as oxalic acid, fumaric acid or other pharmaceutically acceptable acids. 2-aminoethoxyammine is a known product (Bruno, I. et al. Helv. Chim. Acta, 1962, 45, 358).

On varying the hydroxylamine used, in the last step, compounds of general formula (I) described in the previously cited patent application are obtained.

In this case, the hydroxylamine used has general formula (II):

(II)

in which: n=1–3; $R^1$ and $R^2$ have the meanings described previously.

The hydroxylamines with general formula (II) can be used as free bases or in forms salified with inorganic acids such as hydrochloric acid or sulphuric acid.

The hydroxylamines with general formula (II) are known products, which are often available commercially or can be prepared from commercially available products using standard methods.

The advantages in terms of costs and time which can be achieved with the process that is the subject matter of the invention are therefore obvious.

The process which is the subject matter of the invention described herein is further illustrated by the following examples.

EXAMPLE 1

Step A

To a solution of dehydroepiandrosterone (30.0 g) in 450 mL of THF maintained under a nitrogen atmosphere and at a temperature of −10° C. was added the complex BH₃.THF 1M in THF (260 mL). On completing the addition, the temperature was allowed to rise once again to ambient temperature; after 3 h 500 mL of H₂O were added and then NaBO₃.4H₂O (31.4 g).

The reaction was left to stir for one night.

The precipitate formed was filtered, washed with THF and eliminated. The aqueous and organic phases were separated, NaCl was added to the aqueous phase and this was re-extracted with THF (3×200 mL). The merged organic phases were anhydrified with NaCl and Na₂SO₄ and evaporated under reduced pressure to obtain the crude product, which was crystallised by AcOEt/MeOH and then filtered and washed with AcOEt. Approximately 21 g of androstane-3β,6α,17β-triol 9 were obtained (known product: Nicholson, S. H., Turner, A. B. *J. Chem. Soc., Perkin Trans.* 1, 1976, 1357).

The analytical results are in agreement with those reported in the literature.

EXAMPLE 2

Step B

To a solution of androstane-3β,6α,17β-triol 9 (18.6 g) in 335 mL of acetone, was added an excess of Jones reagent (74 ml), maintaining the temperature below 40° C. under stirring.

Five minutes after completing the addition, the excess oxidant was eliminated with 10 mL of i-PrOH; after a few minutes the suspension was filtered, the salts were washed with acetone and the washings added to the main filtrate. The solution was then evaporated dry and the solid residue treated with H₂O and extracted with AcOEt (300 mL and 3×100 mL). The merged organic phases were washed with H₂O (100 mL), a 5% NaHCO₃ solution (100 mL), H₂O (100 mL), anhydrified with Na₂SO₄ and vacuum concentrated. 13.6 g of androstane-3,6,17-trione 10 were obtained (known product: Amendolla C. et al., *J. Chem. Soc.*, 1954, 1226).

The analytical results are in agreement with those reported in the literature.

EXAMPLE 3

Step C

To a solution of androstane-3,6,17-trione 10 (10.0 g) in 200 mL of THF was added drop-wise by rapid drip a solution of 2-aminoethoxyamine dihydrochloride in H₂O (3.92 g, in 50 mL). The mixture was left to react at ambient temperature for 1.5 h. The reaction was washed adding NaCl and maintaining it under stirring for approximately 10 minutes; the phases were separated and the aqueous phase was re-extracted with THF (2×100 mL). Anhydification was done with Na₂SO₄ and the solvent was evaporated, obtaining an oily residue which was treated with CH₂Cl₂ (200 mL circa) and washed with a saturated solution of NaCl (3×30 mL). The reaction mixture was anhydrified again with Na₂SO₄ and the solvent evaporated, obtaining a crude product (13.8 g approx.), which was crystallised by AcOEt (55 mL) to yield 7.0 g of the product desired, (E,Z) 3-(2-aminoethoxyimino)-androstane-6,17-dione (PST 2744) as a hydrochloride, with a melting point of 208–210° C.

What is claimed is:

1. A process for the preparation of a compound of general formula (I)

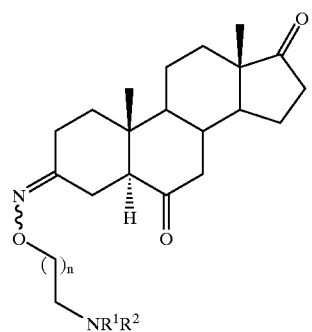

in which:

n=1–3; $R^1$ and $R^2$, which may be the same or different, are hydrogen or $C_1$–$C_6$ alkyl or together form a 5 or 6 member saturated heterocycle, optionally containing a second heteroatom selected from the group consisting of oxygen, sulfur or nitrogen, said process comprising the steps of:

(a) introducing a hydroxyl group in position 6α of the steroid skeleton and at the same time reducing the ketone function in position 17 thereby obtaining a compound of the formula:

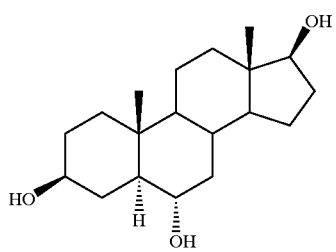

from dehydroepi-androsterone;

(b) oxidating simultaneously the three hydroxyl groups present in the compound of step (a) to produce a compound of the formula:

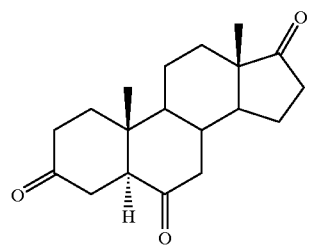

and thereafter (c) selectively oximating the ketone group in position 3 of the compound of step (b) with hydroxylamine, optionally in salified form, with a compound of general formula (II)

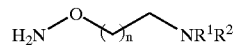
(II)
in which n=1–3 and $R^1$ and $R^2$ are as defined above.
2. The process according to claim 1, in which the oximation step (c) is accomplished using 2-aminoethoxy-amine, optionally in salified form, to yield (E,Z)-3-(2-aminoethoxyimino)-androstane-6,17-dione.
3. The process according to claim 1, in which the product is obtained in salified form.
* * * * *